United States Patent

Itsuo et al.

[11] Patent Number: 4,806,659
[45] Date of Patent: Feb. 21, 1989

[54] TANNIN COMPOUNDS

[75] Inventors: Nishioka Itsuo; Nonaka Genichiro; Fujiwara Michihiro; Ueki Showa, all of Fukuoka, Japan

[73] Assignee: Kabushiki Kaisha Tsumura Juntendo, Tokyo, Japan

[21] Appl. No.: 935,230

[22] PCT Filed: Mar. 7, 1986

[86] PCT No.: PCT/JP86/00116
§ 371 Date: Nov. 7, 1986
§ 102(e) Date: Nov. 7, 1986

[87] PCT Pub. No.: WO86/05180
PCT Pub. Date: Sep. 12, 1986

[30] Foreign Application Priority Data
Mar. 8, 1985 [JP] Japan .................. 60-44625

[51] Int. Cl.$^4$ .......................... C07D 311/62
[52] U.S. Cl. .................................. 549/399
[58] Field of Search .................. 549/399; 514/456

[56] References Cited
FOREIGN PATENT DOCUMENTS
56-92283  7/1981  Japan .
58-32875  2/1983  Japan .
0154571  9/1983  Japan .................. 549/399
59-59638  4/1984  Japan .

OTHER PUBLICATIONS
Nonaka et al., Chem. Pharm. Bull, 29, pp. 2862-2870 (1981).
Skakun et al., Farmakal Toksikol, 49, No. 2, pp. 45-48 (1986).

*Primary Examiner*—John W. Rollins
*Assistant Examiner*—W. Catchpole
*Attorney, Agent, or Firm*—Watts, Hoffmann, Fisher & Heinke Co.

[57] ABSTRACT

The invention herein disclosed provides a tannin especially effective as antipsychotic drug for mental disorders such as acute and chronic schizophrenia. This tannin composition is represented by the following general formula:

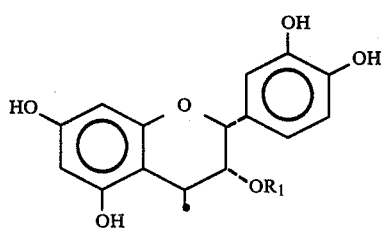

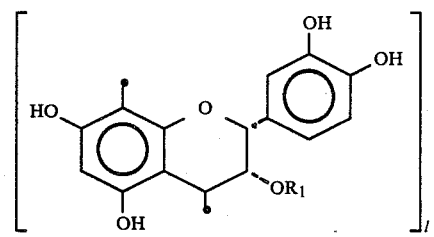

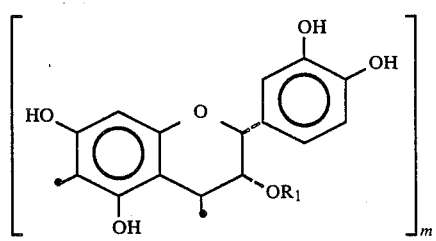

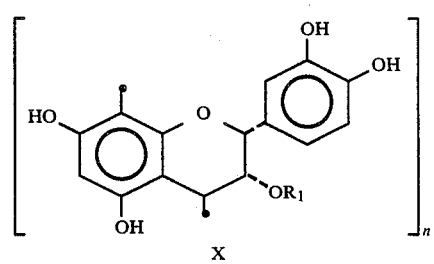

wherein
$l$ is an integer from 0 to 6, m is 0 or 1, n is an integer from 0 to 6, $l+n+m=6$;
$R_1$ is hydrogen or G, G representing the galloyl group

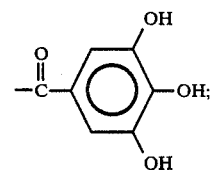

X is

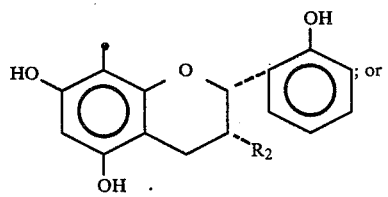

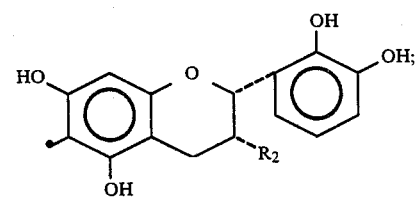

$R_2$ is OH, ... OG, or ... OH; filled dots mean bonding sites, there being no possibility to bond between the mutual fourth positions in each unit; there is only one bonding between the fourth and the sixth position; and there is a total of three galloyl groups in the tannin.

1 Claims, No Drawings

TANNIN COMPOUNDS

TECHNICAL FIELD

The present invention pertains to a novel tannin composition and, more particularly, to a novel tannin composition used for treating mental disorders such as acute and chronic schizophrenia and the like.

BACKGROUND ART

Rhei Rhizoma is a kind of crude drug previously known, and used frequently in traditional chinese prescription (Kampo). The Rhei Rhizoma is so far known to possess an antibacterial effect, blood urea nitrogen-decreasing activity and anti-inflammatory effect. In the prior art, in order to obtain substances providing such effects, various compositions and/or compounds such as sennoside A have been isolated from Rhei Rhizoma. However, among the compounds isolated from Rhei Rhizoma, no components usable for treating mental disorders have been previously known at all.

Whereas, the following chemical compounds have been known as antipsychotic drugs used for treating schizophrenia:

Levomepromazine, chlorpromazine and thioridazine showing strong sedative effect; perphenazine, fluphenazine and haloperidol showing strong anti-hallucination and -delution effects; and sulpiride having mild sedative effect, and anti-hallucination and -delution effects. These drugs have been selectively used, according to their respective characteristics, in response to patient's symptoms and the progress of disease. However, it has been well-known that these drugs produce adverse effects which are extrapyramidal syndrome such as muscle rigidity, dyskinesia and parkinsonism, and autonomic symptoms such as salivation, dry mouth and constipation. Consequently, a drug without adverse effects for treating mental disorders has long been desired to be developed.

DISCLOSURE OF INVENTION

Therefore, one of the objects of the present invention is to provide a novel tannin composition.

Another object of the present invention is to provide a novel tannin composition extracted from Rhei Rhizoma.

A further object of the present invention is to provide such novel tannin composition having a potent antipsychotic effect, which can be used for treating acute and chronic schizophrenia, without causing any adverse effects.

These and other objects, together with the advantages thereof over the prior art, will become apparent from the following description and the appended claims.

A tannin according to the present invention is represented by the following general octameric structural formula:

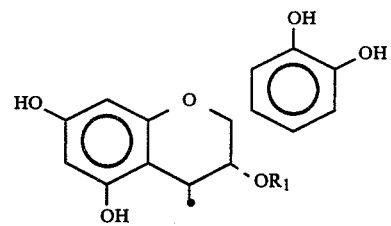

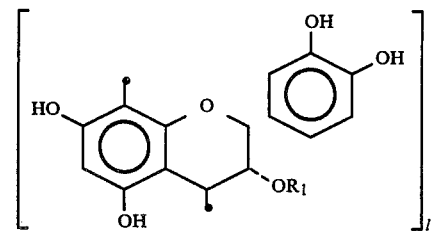

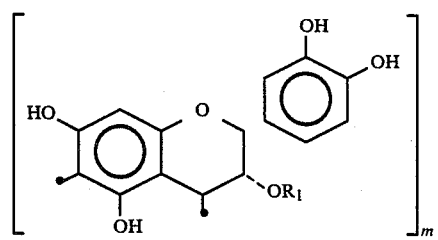

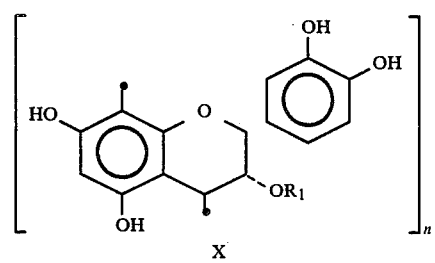

wherein
l is an integer from 0 to 6, m is 0 or 1, n is an integer from 0 to 6, and $l+m+n=6$;

$R_1$ is hydrogen or G, G representing galloyl group

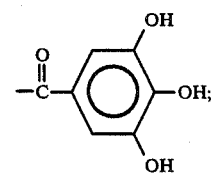

X is

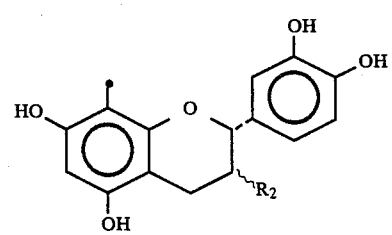

or

-continued

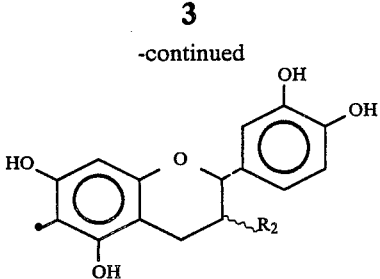

$R_2$ is ◀ OH, ... OG, or ... OH; and filled dots ● mean bonding sites, and there is no possibly to bond between the mutual fourth positions in each unit, and there is only one bonding between the fourth position and the sixth position; and there is a total of three galloyl groups in the tannin.

In accordance with the present invention, the above tannin composition may be obtained by the following steps:

obtaining an extractive from Rhei Rhizoma with water or an aqueous solution of an organic solvent;

separating said extractive or its concentrated liquid by gel filtration chromatography using water, an aqueous solution of ethanol, ethanol and methanol sequentially, to obtain a methanolic eluate;

separating said methanolic eluate, its concentrated liquid or dried solid by gel filtration chromatography with a mixture of at least two solvents selected from the group consisting of water, ethanol, methanol and acetone, to obtain an eluate;

subjecting said eluate to high performance liquid chromatography [column: Nucleosil 5C$_{18}$ (Macherey-Nagel) (4×250 mm); mobile phase: 14–80% CH$_3$CN/H$_2$O (25 mM oxalic acid); flow rate: 1 ml/min; column temperature: 40° C.], to separate and obtain a fraction eluted at the retention time from 10 to 25 minutes; and removing the solvent from said eluted fraction.

It is also disclosed, according to the present invention, that the above tannin composition is effective in treating mental disorders such as acute and chronic schizophrenia.

BEST MODE FOR CARRYING OUT THE INVENTION

Rhei Rhizoma used in order to obtain a novel tannin composition according to the present invention is commercially available in the form of crude drugs. The original plant of Rhei Rhizoma is a perennial herb belonging to the Polygonaceae family.

Rhei Rhizoma is first extracted by using water or an aqueous solution of an organic solvent, in order to obtain a desired extractive. This extraction process is carried out at the temperature ranging from room temperature to the boiling point of the extracting solvent to be used. Preferably Rhei Rhizoma may be previously reduced to powders, and in this case high extracting efficiency is achieved. Ethanol, methanol, acetone and etc. are preferable as an extracting organic solvent. It is most recommendable to extract using water for 12 through 24 hours at room temperature. In this manner, the resultant extractive contains a minimum of contaminants other than the desired tannin composition of this invention. Repeating the above extraction process 2 through 4 times brings higher extracting efficiency.

The extractive obtained in the above extracting process may be directly subjected to gel filtration chromatography. Alternatively, the extractive may be concentrated prior to being subjected to the chromatography. Preferable examples of gel used in the gel filtration chromatography are Sephadex ® (Pharmacia Fine Chemicals), MCI gel ® (Mitsubishi Kasei) and μ-Bondapak ® (Waters Associates). Water, an aqueous solution of ethanol, ethanol and methanol are sequentially employed as eluting solvents. In case where MCI gel ® or μ-Bondapak ® is used, methanol may be introduced immediately after water introduction. By this procedure, a methanol eluate is obtained.

The methanol eluate obtained in the above eluting process, its concentrated liquid or dried solid is subjected to gel filtration chromatography. An eluate is obtained in the chromatography by using a mixture of at least two solvents selected from the group consisting of water, ethanol, methanol and acetone. Preferable examples of packing gels employed are Sephadex ® (Pharmacia Fine Chemicals), MCI gel ® (Mitsubishi Kasei) and μ-Bondapak ® (Waters Associates). In case where Sephadex ® is used as a packing gel, a mixture of ethanol, water and acetone is the most suitable solvent. In case where MCI gel ® is packed in the column, a mixture of ethanol-water or methanol-water is the most suitable solvent. In this manner, a desired eluate is obtained.

The eluate obtained in the preceding process is subjected, as it is, to high performance liquid chromatography [column: Nucleosil 5C$_{18}$ (Macherey-Nagel) (4×250 mm); mobile phase: 14–80% CH$_3$CN/H$_2$O (25 mM oxalic acid); flow rate: 1 ml/min; column temperature: 40° C.].

And then a fraction eluted at the retention time from 10 to 25 minutes is separated to obtain a desired eluted fraction.

Lastly, the eluting solvent is removed by evaporation at reduced pressure from the fraction eluted in the preceding process, resulting in the separation of tannin composition according to the present invention.

Preferably examples of the pumps used in the above high performance liquid chromatography are TOYOSODA CCPD Dual Pump (Toyosoda Kogyo), Waters 6000A-type Pump (Waters Associates), JASCO TRI ROTAR-VI Pump (Nihon Bunko Kogyo), Hitachi 655-type Pump (Hitachi Seisakusho), etc. In addition, preferable examples of the detectors used in the high performance liquid chromatography are TOYOSODA UV-8 Model II (Toyosoda Kogyo), Waters Model 440 Absorbance-detector (Waters Associates), JASCO UVIDEC-100-VI UV Spectrometer (Nihon Bunko Kogyo), Hitachi 638-41-type Variable-wavelength UV Monitor (Hitachi Seisakusho), etc. A suitable absorption wavelength in the detection is 280 mm. A more detailed explanation regarding preparation of the tannin composition of the present invention is provided with the example hereinbelow.

EXAMPLE

Powdered Rhei Rhizoma (3 kg) was steeped in purified water (15–25 liters), and extracted at room temperature for 12–24 hours. The same extraction process was repeated three times to produce three same extractives. The combined extractives were concentrated to 4 liters at reduced pressure. This concentrate was subjected to column chromatography [Sephadex ® LH-20 (Pharmacia Fine Chemicals 25–100 micrometers), (11×50 cm)]. The column was eluted using water, water-ethanol (1:1), ethanol, methanol, aceton-water (1:1) (20 liters each) sequentially, and each fraction was obtained. The yields of these four fractions were 525, 193, 67, 47 grams, respectively.

The fraction No. 4 (36 grams) was subjected to column chromatography [Sephadex® LH-20, (5.8×50 cm)], and the column was eluted with a mixture of ethanol-water-aceton (1:0:0, 19:0.5:0.5, 18:1:1, 17:1.5:1.5, 16:2:2, 15:2.5:2.5, 14:3:3, 13:3.5:3.5, 12:4:4, 11:4.5:4.5, 10:5:5, 8:6:6, 0:1:1, 4 liters each). The eluate liquid was subjected to a high performance chromatography [pump: TOYOSODA CCPD Dual Pump; detector: TOYO SODA UV-8 Model II; column: Nucleosil 5C$_{18}$ (Macherey-Nagel) (4×250 mm); mobile phase: 14–80% CH$_3$CN/H$_2$O (25 mM oxalic acid); flow rate: 1 millimeter/min; column temperature: 40° C.; absorption: 280 nm]. The fraction eluted at the retention time from 10 to 25 minutes was separated. The solvent was removed from the separated fraction by evaporation and 15.6 grams of the tannin composition of the present invention, was finally obtained.

Pharmacological Assessment

The test substance was dissolved in saline (0.9% NaCl) and administered i.p. or p.o. to rats in a single-dose study. To control group, only salines (i.p.) or water (p.o.) was administered.

EXAMPLE 1

Eight male SD rats, 5–6 weeks of age, were used for each i.p. dose (0, 5, 10, 20 and 50 mg/kg).

In the open field test, the test substance reduced the locomotor activity and rearing dose-dependently.

These suggest that the test substance has sedative effect.

EXAMPLE 2

Eight male SD rats, 5–6 weeks of age, were used for each i.p. dose (0, 1 and 2 mg/kg). The test substance was administered 1 hour prior to d-methamphetamine (1 mg/kg, s.c.). d-Methamphetamine is known to produce abnormal behavioral in animals. The test substance at 1 and 2 mg/kg inhibited d-methamphetamine-induced locomotor hyperactivity. (Graphs 1A and 1B)

Therefore, it is clearly indicated that the test substance has anti-methamphetamine effect. This inhibitory effect is twice as potent as chlorpromazine.

Graph 1A ambulation/3 minutes

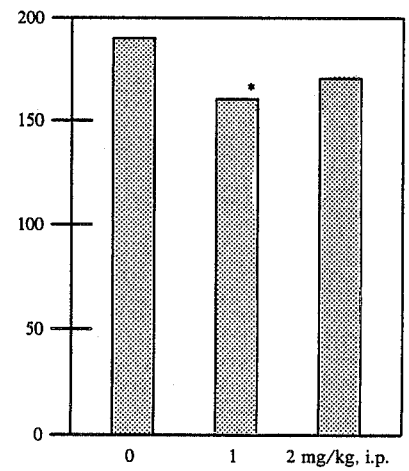

-continued
Graph 1A $*p < 0.05$

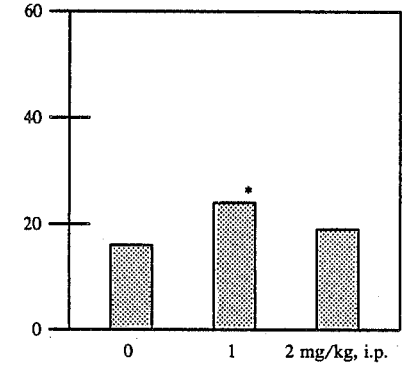

Graph 1B
rearing/3 minutes $*p < 0.05$

EXAMPLE 3

Ten male Wistar-King A rats for each group, 5–6 weeks of age, were used. The olfactory bulbs of these rats were removed (O.B. rats), which resulted in the appearance of aggressive behavior. The effects of the test substance on agressive behavior induced by olfactory bulbectomy were evaluated by the following 6 parameters;

1. attack: attack response to a rod presented in front of the snout.
2. tapping: jumping or startle response to tapping on the back
3. pinching: flight response or attack response to tail pinching.
4. capture: struggle response to capturing.
5. vocal: vocalization during the observation period.
6. muricide: mouse killing behavior.

These parameters were graded on a 0–4 basis (score 0: no response—score 4: maximal response). The total score was made by summing up each score of 6 parameters. The test substance i.p. administered at 1, 2 and 5 mg/kg significantly lowered total score of aggressive behaviors (Graph 2). This effect continued for up to about 6 hours. The test substance orally administered at 10 and 20 mg/kg showed similar inhibitory effects to the above by i.p. administration.

These results suggest that the test substance has anti-aggressive effect.

This inhibitory effect is 10 times as strong as haloperidol and twich as strong as chlorpromazine.

During the above 3 experiments, catalepsy, ataxia and muscle relaxation were not observed.

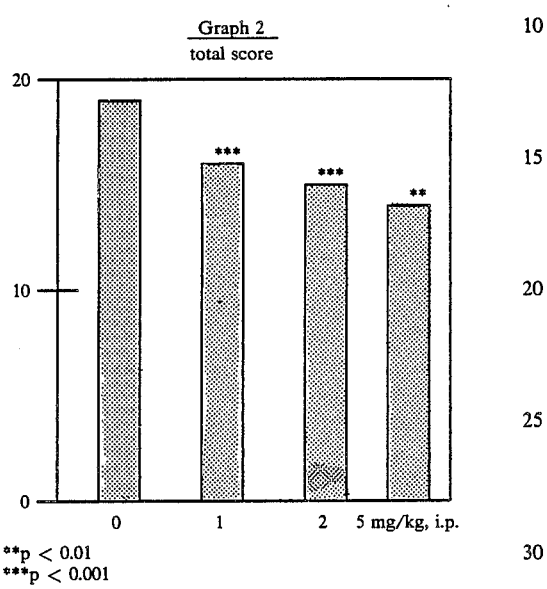

Graph 2
total score

** $p < 0.01$
*** $p < 0.001$

Toxicological Assessment $LD_{50}$ of the test substance in mice is as follows. The test substance was dissolved in saline except for oral administration (in water).

| Animal: ddY male mice (n = 10), 4 weeks of age. | |
| --- | --- |
| Route of administration | $LD_{50}$ (mg/kg) |
| intravenously administration | 70.9 |
| intraperitoneal administration | 369.4 |
| oral administration | >1000 |
| subcutaneous administration | >1000 |

The overall results obtained indicate the possibility that the test substance may be useful for some psychiatric disorders in human.

Practical Use

Medicines in the wide variety forms such as liquid, powder, granulated powder, pill, tablet, enteric coated tablet and capsule may be produced in the conventional manner by using this tannin composition together with suitable solvent, excipient, adjuvant, etc. The above medicines may be compounded into other medicinal active ingredient in case of prescribing. For oral administration, medicines in the form of liquid, powder, granulated powder, pill, tablet, enteric coated tablet and capsule may be prescribed by using at least one excipient such as starch, lactose, sucrose, mannitol and carboxymethylcellulose. The above medicines may also be produced by using brighteners such as magnesium stearic acid, sodium lauric acid and talc; binders such as dextrin, crystalline cellulose, polyvinyl pyrrolidone and gelatin; and breaking agents such as potato starch and carboxymethylcellulose. This tannin composition may be administered as suspension, emulsion, syrup and elixior, which may contain taste and odor correcting agent and coloring agent.

In case of production of injecting medicines, there may be used diluents such as an injecting vegetable oil, propylene glycol and polyethylene glycol. Further, isotonic agents, stabilizer, antiseptics and anodynes may be added if necessary. It is preferable to dissolve the injecting medicines in a sterilized injecting medium. All percentage and ratios stated herein are by volume unless otherwise expressly indicated.

I claim:

1. A tannin represented by the following general octameric structural formula:

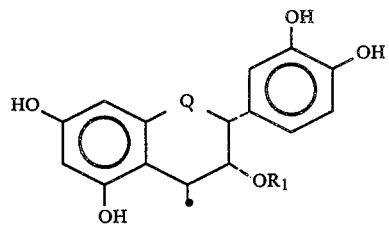

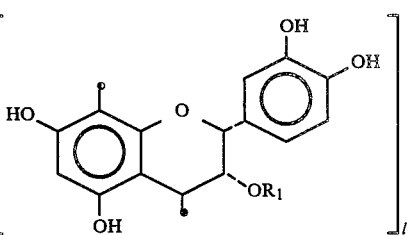

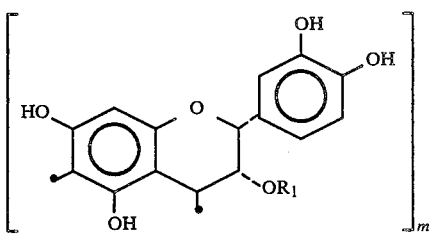

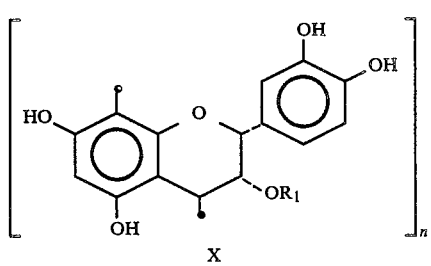

X wherein
l is an integer from 0 to 6, m is 0 or 1, n is an integer from 0 to 6, and $l+m+n=6$;
$R_1$ is hydrogen or G, G representing galloyl group

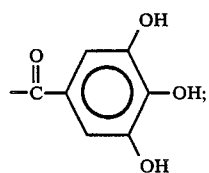

X is
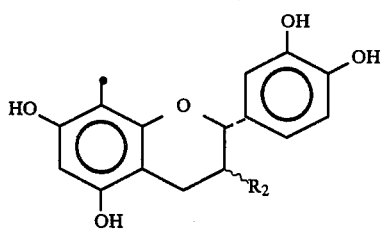
or
-continued
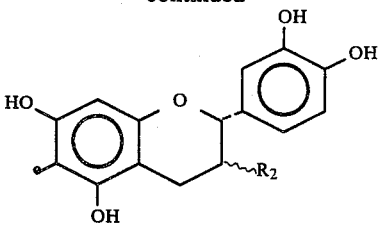
$R_2$ is ◀ OH, ... OG, or ... OH; and filled dots ● mean bonding sites, and there is no possibility to bond between the mutual fourth positions in each unit, and there is only one bonding between the fourth position and the sixth position; there being a total of three galloyl groups in the tannin.
* * * * *